US008889067B1

(12) United States Patent
Weaver

(10) Patent No.: US 8,889,067 B1
(45) Date of Patent: Nov. 18, 2014

(54) METHOD FOR RESTROOM STALL DEODORIZING

(71) Applicant: Vern Weaver, Wichita, KS (US)

(72) Inventor: Vern Weaver, Wichita, KS (US)

(73) Assignee: Envision Industries, Inc., Wichita, KS (US)

( * ) Notice: Subject to any disclaimer, the term of this patent is extended or adjusted under 35 U.S.C. 154(b) by 0 days.

(21) Appl. No.: 13/902,464

(22) Filed: May 24, 2013

(51) Int. Cl.
*A61L 9/04* (2006.01)
*A61L 2/20* (2006.01)

(52) U.S. Cl.
CPC ................ *A61L 2/20* (2013.01); *Y10S 206/823* (2013.01)
USPC ................ 422/5; 206/225; 206/409; 206/823

(58) Field of Classification Search
CPC ......................................................... A61L 9/04
USPC ............................... 422/5; 206/225, 409, 823
See application file for complete search history.

(56) References Cited

U.S. PATENT DOCUMENTS 5,950,818 A * 9/1999 Paulsen .......................... 206/205
2012/0330265 A1* 12/2012 Germanow et al. ...... 604/385.13

* cited by examiner

*Primary Examiner* — Sean E Conley
(74) *Attorney, Agent, or Firm* — Kenneth H. Jack; Davis & Jack, L.L.C.

(57) ABSTRACT

A method for reducing feminine hygiene product odor within a restroom stall having a disposal bin, the method including providing a case, the case being adapted for storing a plastic bag roll and being adapted for dispensing the bags, the plastic bag roll being fitted for receipt within the case and the plastic bag roll incorporating a chemical deodorizing agent; mounting the case within the stall; receiving the plastic bag roll within the case; outwardly sublimating a first portion of the deodorizing agent from one of the plastic bag roll's bags and into the restroom stall; dispensing one of the bags from the case; donning the one of the bags in the manner of a mitt; grasping the feminine hygiene product and obverting the one of the bags about the feminine hygiene product; and inwardly sublimating a second portion of the chemical deodorizing agent.

18 Claims, 5 Drawing Sheets

METHOD FOR RESTROOM STALL DEODORIZING

FIELD OF THE INVENTION

This invention relates to public and commercial restrooms having women's restroom stalls. More particularly, this invention relates to methods adapted for reducing unwanted odors within such stalls.

BACKGROUND OF THE INVENTION

Sanitary and odor free handling and disposal of used or soiled feminine hygiene products within women's bathroom stalls is often achieved only with difficulty. Such difficulty often arises through hesitancy by women to properly handle such items, the items being left in the stall unbagged. Such modes of disposal often undesirably contribute to restroom stall odor problems.

The instant inventive method solves or ameliorates such women's restroom stall odor problems by providing uniquely integrated and uniquely configured bag and bag dispenser components, and by incorporating usage and handling steps which are performed in conjunction with the provided components for achieving sanitary hygiene product handling and for achieving simultaneous room, bag, and disposal bin deodorization.

BRIEF SUMMARY OF THE INVENTION

The instant inventive method for reducing feminine hygiene product odor within women's restroom stalls preferably includes a step of providing a bag dispensing case which is adapted for storing a roll of plastic bags and which is adapted for dispensing such bags. In a preferred embodiment, the provided case comprises a plastic injection molded substantially rectangular box having a pivoting or hinged front lid or door. According to the method, the provided case is mounted within the women's restroom stall, preferably by fastener attachments to one of the stall's sidewalls.

In a further step of the instant inventive method, a plastic bag roll is provided, such roll being fitted for insertion into and receipt within the case. In a preferred mode of performance of the instant inventive method, the bag roll is integrally plastic injection molded to include an odorant chemical or chemical deodorizing agent which is capable of directly emanating through sublimation from the plastic matrix of the bags into the surrounding ambient atmosphere. The chemical deodorizing agent preferably includes pleasant scents or odors such as orange scent, lemon scent, lilac scent, or rose scent. The chemical deodorizing agent which emanates from the plastic bag roll is preferably of a strength capable of masking unpleasant odors within the bathroom stall. Accordingly, the steps of the instant inventive method include outwardly sublimating a first portion of such chemical deodorizing agent from the plastic bag roll and into the women's restroom stall.

In a further step of the instant inventive method, one of the bags from the plastic bag roll is dispensed from the case, such step preferably being accomplished via a restroom stall occupant's pulling of an exposed bag roll end at a dispensing slot which opens the case.

Upon tearing a single plastic bag away from the roll and away from the case, the occupant may place the opened bag over one of her hands, such placement donning or wearing the bag in the manner of a worn mitt.

Thereafter, the occupant may utilize such bag in the manner of a worn mitt to grasp in a sanitary fashion a used or soiled feminine hygiene product. Thereafter, while the occupant continues to hold such product with the mitt, the occupant may obvert (i.e., turn inside out) the bag about and over the soiled product, causing the hand to exit the mitt and causing such product to be contained within a newly formed interior space.

Upon completion of such bag obverting and product containing step, a second portion of the bag's impregnated chemical deodorizing agent effectively inwardly sublimates for performing deodorization within the bag. Upon a subsequent step of disposal of the bag within a disposal bin within the stall, the bag effectively outwardly sublimates a third portion of the chemical deodorizing agent within the bin for deodorizing therein.

Accordingly, objects of the instant inventive method include reduction of feminine hygiene products induced odor within a women's restroom stall through the performance of method steps as described above in the manners as described above.

Other and further objects, benefits, and advantages of the instant inventive method will become known to those skilled in the art upon review of the Detailed Description which follows, and upon review of the appended drawings.

DETAILED DESCRIPTION OF A PREFERRED EMBODIMENTS

Figure 1:
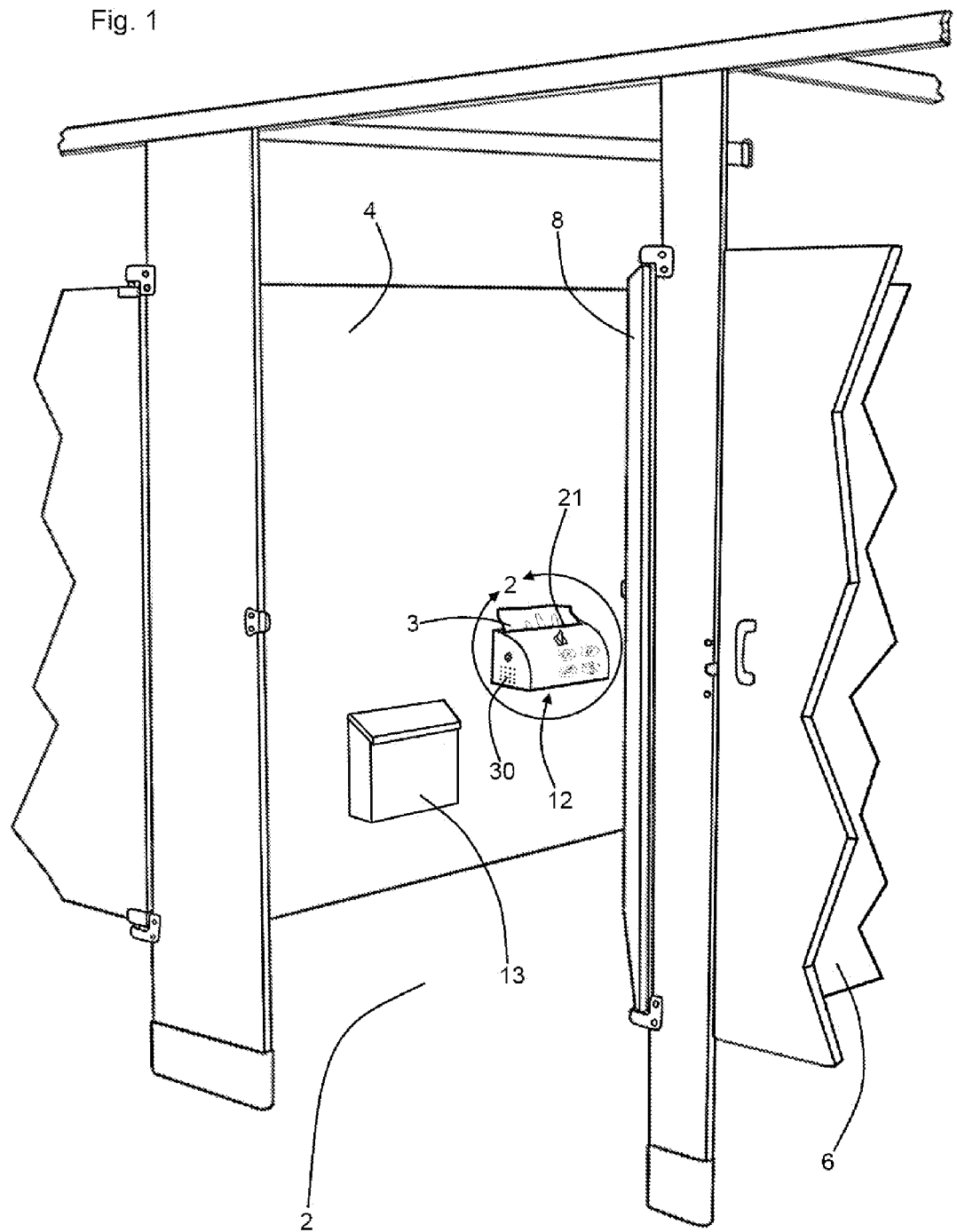
FIG. 1 presents a view of a women's restroom stall within which the instant inventive method is typically performed.

Referring now to the drawings, and in particular to Drawing FIG. 1, a women's restroom stall is depicted, such stall having an interior space 2, right and left side walls 4 and 6, and a door 8. A conventional feminine hygiene product disposal bin 13 is fixedly attached to sidewall 4. Steps of the inventive method for reducing feminine hygiene product odor are performed within the depicted restroom stall.

According to the instant invention, referring simultaneously to FIGS. 1-4, a case 12 is preferably provided. The case 12 is preferably substantially rectangularly configured and is preferably formed via plastic injection molding. Suitably, the case 12 may be fabricated of sheet stainless steel. The case 12 has a floor 20, left and right side walls 14 and 16, and a back wall 18. A door or lid 22 is preferably pivotally attached at the front edge of floor 20 by hinges 24 and 26. Upon pivoting movement closure of the door 22 from the opened position depicted in FIG. 3 to the closed position depicted in FIG. 2, the distal end 23 of the door 22, in combination with the upper end 19 of the back wall 18, forms and defines a laterally extending bag dispensing slot 21. Upon such closure of the door 22, slot 21 effectively further functions as an odorant or chemical deodorizing agent emitting port. Suitably, the provided case 12 may further include side wall fragrance emitting ports 30. Such ports 30 may be suitably positioned upon other walls of the case 12. In a preferred embodiment, the case includes a key lock 32 and latch 34 combination for preventing unauthorized access into the interior of the case 12.

Figure 3:
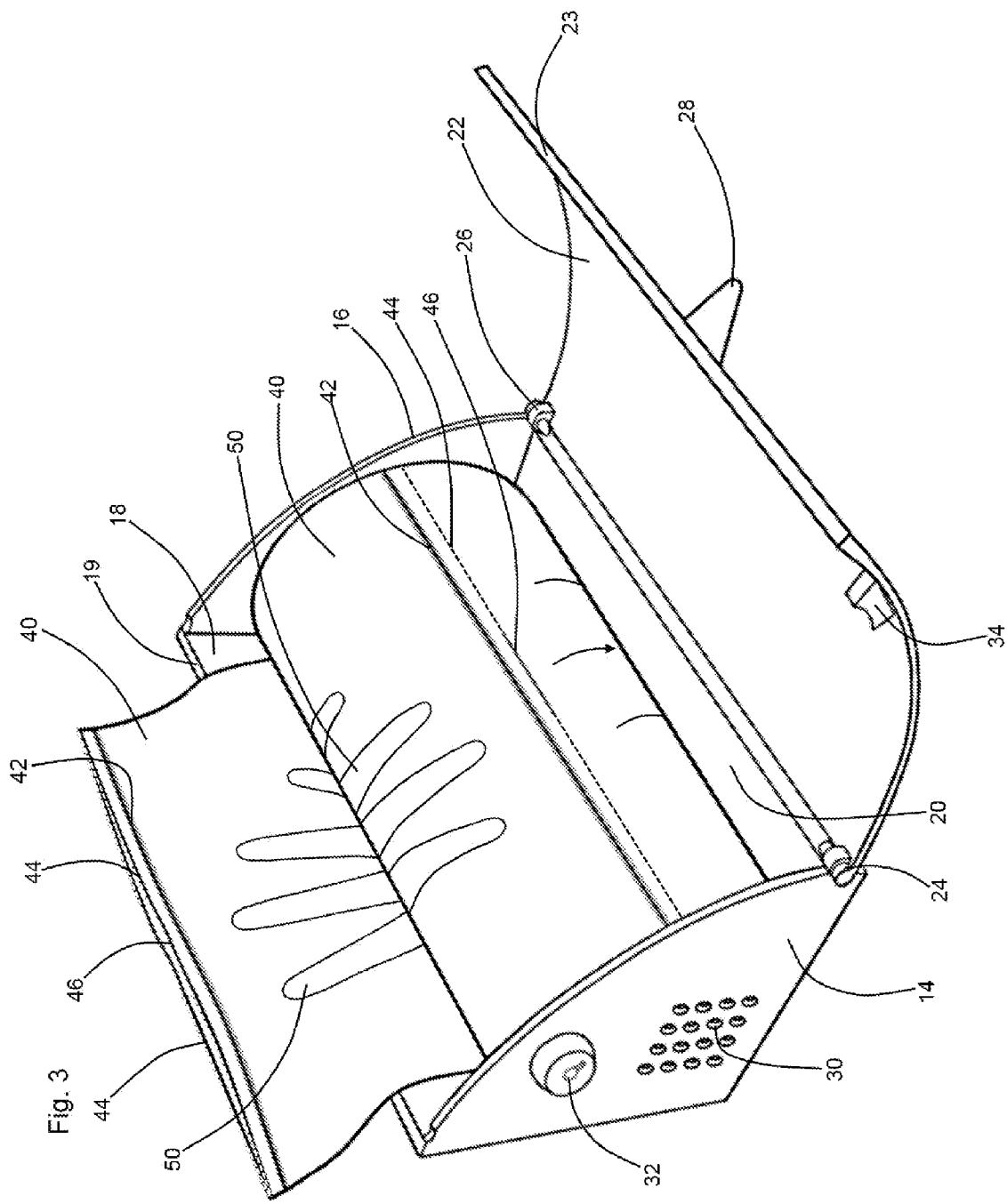
FIG. 3 redepicts the case of FIG. 2, the view of FIG. 3 showing the case's door pivoted to an open position.

Referring to FIG. 3, a roll of plastic bags 40 is preferably provided. Such bag roll preferably including an integrally molded odorant or chemical deodorizing agent. In the provision of such agent, fragrance or odorant chemicals are preferably added to an organic oil or wax based substrate that is homogeneously blended with a variety polymers containing an appropriate proportion of calcium carbonate, such proportion preferably being 1%-2% by weight. The calcium carbonate is preferably molded with the plastic and oil or wax substrate for the purpose of functioning as a binding agent which allows for a long lasting chemical deodorizing agent emission, and allows for even distribution of the fragrance or odorant along the surfaces of the plastic substrate.

The bag roll providing step of the instant inventive method preferably further provides within the plastic matrix of the bags an anti-microbial additive. In the preferred embodiment, such additive comprises an inorganic powder characterized by a relatively small particle size between one and two microns. In the preferred embodiment, the anti-microbial additive constitutes a silver ion releasing chemical such as silver iodide which is resistant to chemical breakdown at temperatures up to 600° Fahrenheit.

Figure 4:
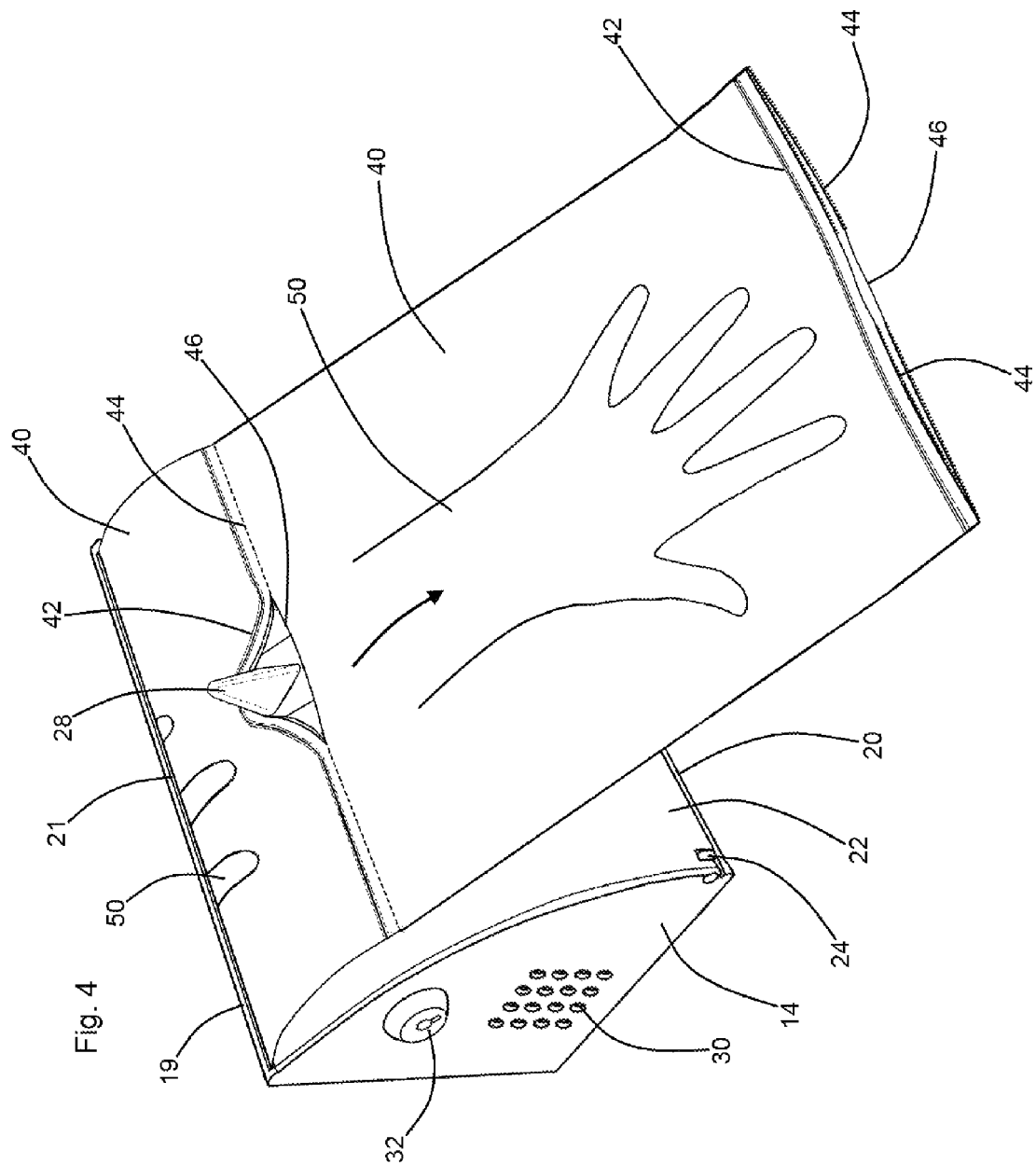
FIG. 4 alternatively redepicts the case of FIG. 2, the view of FIG. 4 showing a dispensed bag and engagement of a bag separately hook.

Referring simultaneously to FIGS. 3 and 4, the rolled bags 40 are preferably formed via a continuous series of heat fusion weld and tear line combinations, each heat fusion weld 42 extending laterally and forming a floor of one of the bags 40, and each tear line 44,46 extending laterally and forming, upon tearing, an opening of one of the bags 40. In the preferred mode of performance of the method, each tear line 44,46 includes a central lance cut section 46 for engagement with a bag tearing hook 28, such hook being fixedly attached to and extending outwardly from the outer surface of door 22.

Referring to FIG. 4, each of the bags 40 preferably includes printed hand insertion indicia, such indicia preferably comprising human hand silhouettes 50. Such indicia 50 serves a function of prominently indicating to occupants of the stall that one of the intended functions of the bag 40 is use as a mitt.

Referring to FIG. 1, in performance of the instant inventive method, an occupant within the interior 2 of the depicted women's restroom stall may continuously positively experience the air scenting and deodorizing effect of first portions of the chemical deodorizing agent which sublimate and emit into the atmosphere from exposed bag end 3, from case dispenser slot 21, and/or from fragrance emitting ports 30. In an event of the occupant's need for handling and disposal of a feminine hygiene product, the occupant may initially grasp the upwardly exposed end 3 of bag 40, and may pull the bag 40 outwardly therefrom, causing the smoothly curved distal end of hook 28 to slide over the undersurface of bag 40. Such pulling and sliding motion preferably continues until hook 28 reaches lance cut 46. Extension of the hook 28 through lance cut 46 effectively engages the hook 28 with the next successive bag 40. Such hook engagement allows continued pulling upon bag 40 to tear the bag away along tear line 44, releasing the bag and creating a hand receiving opening.

Figure 5:
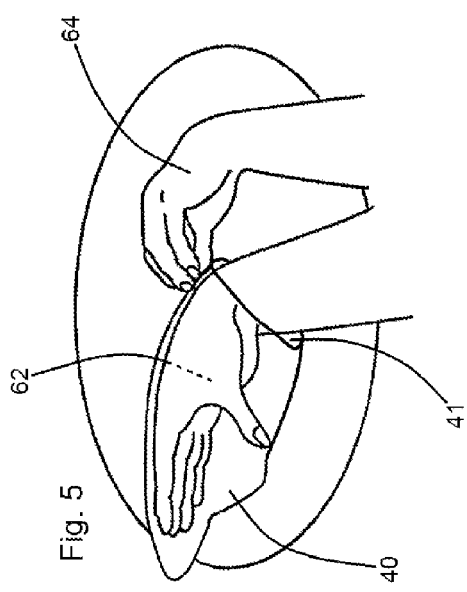
FIGS. 5-8 depict manual usage steps of the instant inventive method.

Thereafter, referring simultaneously to FIGS. 4 and 5, such occupant may splay the edges of tear line 44,46 away from each other to form a bag opening 41, and her hand 62 may thereafter be inserted therein. Immediately prior to the performance of such hand insertion step, such occupant typically views the silhouette hand image 50 and its associated directional arrow, and the occupant is thereby directed and encouraged to perform such hand insertion.

Figure 6:
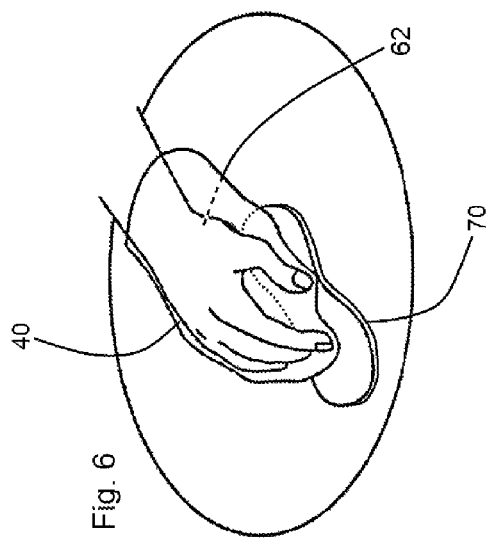

Thereafter, the occupant may utilize the donned or worn bag 40 in the manner of a mitt, and in a sanitary and antiseptic fashion as indicated in FIG. 6, the occupant may then grasp a used or soiled feminine hygiene product 70. Thereafter, referring to FIG. 7, the occupant may use both hands 62 and 64 for obverting or turning inside out the bag 40, such obversion of the bag 40 effectively producing a new interior bag space 41A for containing product 70. Upon such bag obversion, a second portion of the chemical deodorizing agent residing within the matrix of the bag 40 advantageously sublimate or emanates inwardly into the newly formed bag space 41A for deodorizing upon and about product 70. Anti-microbial agents within such bag matrix additionally reduce and resist growth and multiplication of bacteria, further reducing odors within the interior 41A of the bag 40.

Figure 7:
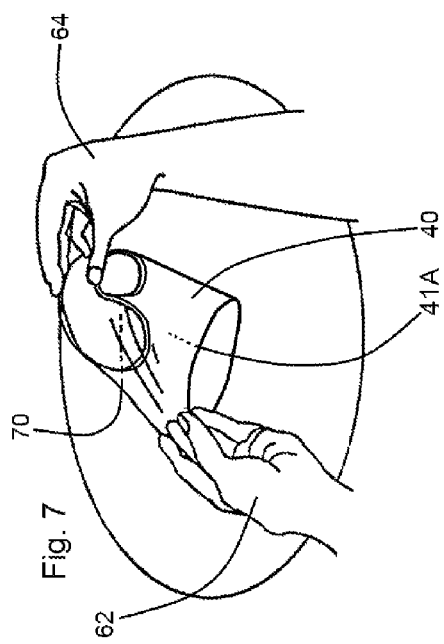
Figure 8:
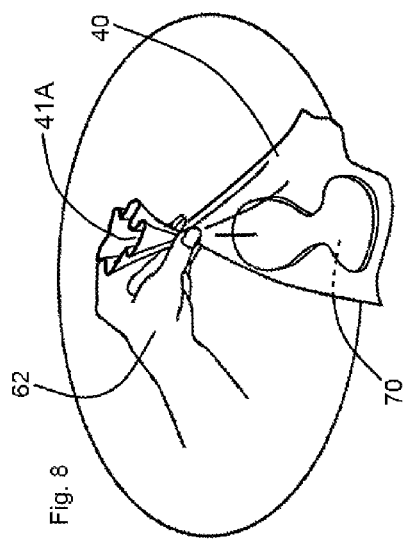

Referring simultaneously to FIGS. 1, 7, and 8, the occupant may thereafter dispose of the bag 40 containing product 70 within disposal bin 13. Upon such disposal, a third portion of the chemical deodorizing agent advantageously emanates into the interior of the bin, blocking and eliminating odors therein.

Figure 2:
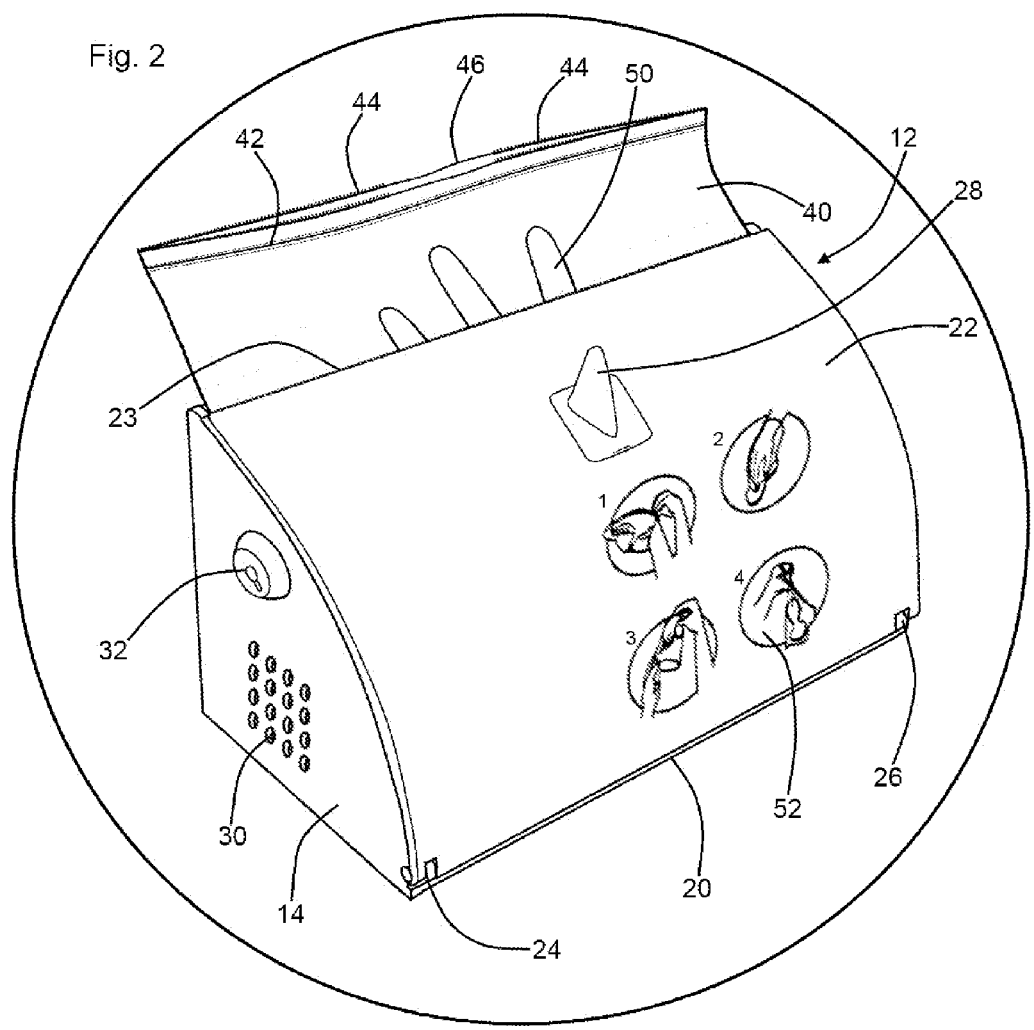
FIG. 2 is a perspective view of a case which is provided in accordance with the instant inventive method.

Referring to FIG. 2, in a preferred mode of performance of the instant invention, the outer surface of the door 22 of the case 12 preferably displays usage step indicia 52, such indicia preferably graphically suggesting and explaining to stall occupants the invention's donning, grasping, obverting, and disposing steps.

The instant inventive method advantageously causes each of the bags 40 among the bag roll to multiply function for restroom stall space deodorizing, for sanitary obverting handling and encapsulation of soiled feminine hygiene products, for bag interior deodorization of contained feminine hygiene products, and for disposal bin deodorization.

While the principles of the method of the invention have been made clear in the above illustrative embodiment, those skilled in the art may make modifications to the method steps including their identity, character, and sequence of performance without departing from those principles. Accordingly, it is intended that the description and drawings be interpreted as illustrative and not in the limiting sense, and that the invention be given a scope commensurate with the appended claims.

The invention hereby claimed is:

1. A method for reducing feminine hygiene product odor within a restroom stall, said stall having a disposal bin, the method comprising steps of:
   (a) providing a case, the case being adapted for storing a provided plastic bag roll and being adapted for dispensing the bags, the plastic bag roll being fitted for receipt within the case and the plastic bag roll comprising a chemical deodorizing agent;
   (b) mounting the case within the restroom stall;
   (c) receiving the plastic bag roll within the case;
   (d) outwardly sublimating a first portion of the chemical deodorizing agent from one of the plastic bag roll's bags and into the restroom stall;
   (e) dispensing one of the bags from the case;
   (f) donning one of the bags in the manner of a worn mitt;
   (g) grasping the feminine hygiene product and obverting the one of the bags about the feminine hygiene product; and
   (h) inwardly sublimating a second portion of the chemical deodorizing agent from the one of the bags.

2. The method for reducing feminine hygiene product odor within a restroom stall of claim 1 further comprising steps of disposing of the one of the bags within the disposal bin, and outwardly sublimating a third portion of the chemical deodorizing agent from the one of the bags and into the disposal bin.

3. The method for reducing feminine hygiene product odor within a restroom stall of claim 2 wherein the case providing step includes a provision of hinged access door having a distal end, the case's adaptation for dispensing the bags comprising a slot, the slot being bounded by the hinged access door's distal end.

4. The method for reducing feminine hygiene product odor within a restroom stall of claim 3 wherein the case providing step includes a provision of a key operated latch adapted for resisting unauthorized openings of the hinged access door.

5. The method for reducing feminine hygiene product odor within a restroom stall of claim 1 wherein the providing a plastic bag roll comprising an chemical deodorizing agent step configures the plastic bags to include an organic oil or wax based substrate including a fragrance chemical.

6. The method for reducing feminine hygiene product odor within a restroom stall of claim 5 wherein the providing a plastic bag roll comprising an chemical deodorizing agent step further configures the plastic bags to include a homogeneous blend of the organic oil or organic wax based substrate with a calcium carbonate binding agent.

7. The method for reducing feminine hygiene product odor within a restroom stall of claim 1 wherein the plastic bag roll providing step configures the plastic bags to include an antimicrobial agent.

8. The method for reducing feminine hygiene product odor within a restroom stall of claim 7 wherein the antimicrobial agent comprises a silver ion releasing chemical compound.

9. The method for reducing feminine hygiene product odor within a restroom stall of claim 8 wherein the silver ion releasing chemical compound comprises silver iodide.

10. The method for reducing feminine hygiene product odor within a restroom stall of claim 3 further comprising a step of displaying within the restroom stall bag usage and disposal steps indicia.

11. The method for reducing feminine hygiene product odor within a restroom stall of claim 10 wherein the display of the bag usage and disposal steps indicia graphically depicts a restroom stall occupant's hands performing the donning, grasping, obverting, and disposing steps.

12. The method for reducing feminine hygiene product odor within a restroom stall of claim 11 wherein the hinged access door has an outer surface, and wherein the graphic depiction of the donning, grasping, obverting, and disposing steps resides upon said surface.

13. The method for reducing feminine hygiene product odor within a restroom stall of claim 3 wherein the plastic bag roll's plastic bags are defined by a series of weld and tear line combinations, each of said combinations' welds extending laterally at the floor of one of the bags, and each of said combinations' tear lines extending laterally at one of the bags' openings.

14. The method for reducing feminine hygiene product odor within a restroom stall of claim 13 wherein the hinged access door has an outer surface and a has bag hook fixedly attached to and extending outwardly from said outer surface, each of the bags' weld and tear line combinations' tear lines comprising a central hook engaging lance cut.

15. The method for reducing feminine hygiene product odor within a restroom stall of claim 14 wherein the providing a plastic bag roll step includes provisions of hand insertion directing indicia printed upon one of the bag's outer surfaces.

16. The method for reducing feminine hygiene product odor within a restroom stall of claim 15 wherein each hand insertion directing indicia comprises a silhouette of a human hand.

17. The method for reducing feminine hygiene product odor within a restroom stall of claim 1 wherein the providing a case step provides a plurality of fragrance outlet ports opening the case.

18. The method for reducing feminine hygiene product odor within a restroom stall of claim 17 wherein the outwardly sublimating a first portion of the chemical deodorizing agent step emanates such agent through the plurality of fragrance outlet ports.

* * * * *